United States Patent
Dusbabek et al.

(10) Patent No.: US 12,226,589 B2
(45) Date of Patent: Feb. 18, 2025

(54) MULTI-LUMEN SHAFT USED WITH ENDOSCOPIC DEVICE

(71) Applicant: Conmed Corporation, Largo, FL (US)

(72) Inventors: Andrew Joseph Dusbabek, Dayton, MN (US); Scott Arvin Olson, Princeton, MN (US); Christen Andrew Springs, Houston, TX (US); Isaac Raijman, Houston, TX (US)

(73) Assignee: Conmed Corporation, Largo, FL (US)

( * ) Notice: Subject to any disclaimer, the term of this patent is extended or adjusted under 35 U.S.C. 154(b) by 0 days.

(21) Appl. No.: 18/342,274

(22) Filed: Jun. 27, 2023

(65) Prior Publication Data

US 2023/0338699 A1    Oct. 26, 2023

Related U.S. Application Data

(62) Division of application No. 13/843,982, filed on Mar. 15, 2013, now Pat. No. 11,684,747.

(51) Int. Cl.
*A61M 25/00* (2006.01)
*A61B 1/015* (2006.01)
*A61M 31/00* (2006.01)

(52) U.S. Cl.
CPC ......... *A61M 25/0032* (2013.01); *A61B 1/015* (2013.01); *A61M 31/005* (2013.01)

(58) Field of Classification Search
CPC .. A61M 25/0032; A61M 31/005; A61B 1/015
See application file for complete search history.

(56) References Cited

U.S. PATENT DOCUMENTS

| | | | | |
|---|---|---|---|---|
| 6,485,500 B1 * | 11/2002 | Kokish | ............... | A61F 2/013 604/101.03 |
| 2005/0065544 A1 * | 3/2005 | Yamaguchi | ....... | A61M 25/1034 606/192 |
| 2006/0149218 A1 * | 7/2006 | Slater | ................. | A61M 31/00 604/509 |
| 2009/0171369 A1 * | 7/2009 | Gayzik | .............. | A61M 25/1011 606/127 |

* cited by examiner

*Primary Examiner* — Phong Son H Dang
(74) *Attorney, Agent, or Firm* — Bond, Schoeneck & King, PLLC; Frederick J. M. Price

(57) ABSTRACT

Briefly, in accordance with one embodiment, a multi-lumen shaft may be used to with an endoscopic instrument.

5 Claims, 4 Drawing Sheets

50

510
Insert multi-lumen shaft into location distal to object for removal

520
Inflate expandable vessel until expandable vessel approaches threshold volume 530
Dispense contrast dye into proximal and/or distal locations relative to expandable vessel 540
Draw multi-lumen shaft toward said ostium until object passes

*FIG. 5*

MULTI-LUMEN SHAFT USED WITH ENDOSCOPIC DEVICE

CROSS-REFERENCE TO RELATED APPLICATIONS

This application is a divisional of U.S. patent application Ser. No. 13/843,982 filed on Mar. 15, 2013 entitled "MULTI-LUMEN SHAFT USED WITH ENDOSCOPIC DEVICE." Although claimed subject matter is not necessarily limited in scope in this respect, additional example embodiments of MULTI-LUMEN SHAFT USED WITH ENDOSCOPIC DEVICE may be discussed in filed U.S. patent application Ser. No. 13/843,891, now U.S. Pat. No. 9,326,783, titled REMOVAL TOOL FOR USE WITH ENDOSCOPIC DEVICE, by Isaac Raijman et al, herein incorporated by reference in its entirety and assigned to the assignee of currently claimed subject matter.

BACKGROUND OF THE INVENTION

1. Field of the Invention

This disclosure relates to devices that may be used, for example, in association with endoscopic surgery.

2. Description of Related Art

At times, there may be a need to remove an object from one or more of an individual's body orifices, including orifices attached to within the alimentary canal. To remove an object from an orifice within an individual's alimentary canal, such as a stone or other object lodged in a bile duct, for example, endoscopic surgery may be performed. Endoscopic surgery may involve, for example, use of an endoscopic device that may be equipped with a camera that is entered into an individual's mouth and advanced through the alimentary canal until the device is appropriately positioned within the individual's duodenum. However, endoscopic surgery may represent a time-consuming process in which an endoscope and one or more object removal tools may be placed into position by way of a working channel of an endoscope. Once in position, for example, removal of the stone or other object may involve a high degree of cooperation between the endoscope and the removal tools, for example. On occasion, deployment of an endoscope, and the one or more removal tools, may be in need of improvement to bring about decreases in endoscopic surgery costs, decreases in surgeon and support staff time, and to reduce discomfort of the patient undergoing endoscopic surgery.

Claimed subject matter is particularly pointed out and distinctly claimed in the concluding portion of the specification. However, both as to organization and/or method of operation, together with objects, features, and/or advantages thereof, claimed subject matter may best be understood by reference to the following detailed description if read with the accompanying drawings in which:

FIG. 5 is a flow diagram of a process for using an embodiment of a multi-lumen shaft in association with an endoscopic procedure.

Figure 1:
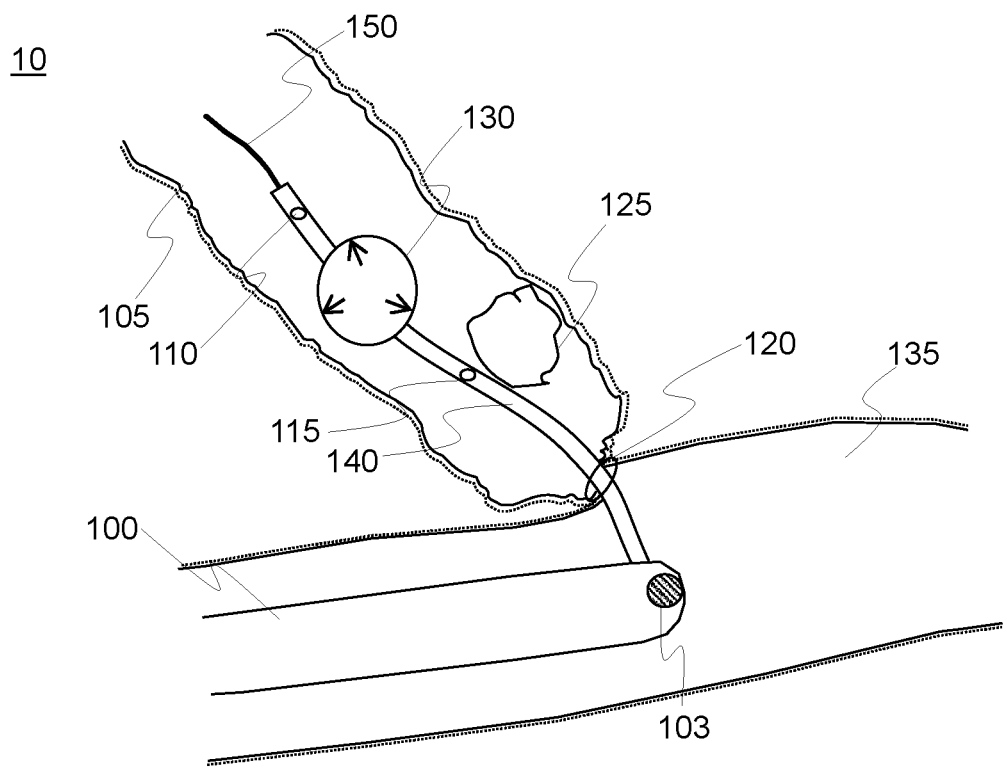
FIG. 1 is a diagram of an embodiment showing use of an endoscopic instrument and multi-lumen shaft deployed in an alimentary canal.

Reference is made in the following detailed description to accompanying drawings, which form a part hereof, wherein like numerals may designate like parts throughout to indicate corresponding and/or analogous components. It will be appreciated that components illustrated in the figures have not necessarily been drawn to scale, such as for simplicity and/or clarity of illustration. For example, dimensions of some components may be exaggerated relative to other components. Further, it is to be understood that other embodiments may be utilized. Furthermore, structural and/or other changes may be made without departing from claimed subject matter. It should also be noted that directions and/or references, for example, up, down, top, bottom, and so on, may be used to facilitate discussion of drawings and/or are not intended to restrict application of claimed subject matter. Therefore, the following detailed description is not to be taken to limit claimed subject matter and/or equivalents.

3. Detailed Description

Reference throughout this specification to "one example," "one feature," "one embodiment," "an example," "a feature," "an implementation," or "an embodiment" means that a particular feature, structure, or characteristic described in connection with the feature, example, or embodiment is included in at least one feature, example, or embodiment of claimed subject matter. Thus, appearances of the phrase "in one example," "an example," "in one implementation," "an implementation," "an embodiment," or "in one embodiment" in various places throughout this specification are not necessarily all referring to the same feature, example, or embodiment. Particular features, structures, or characteristics may be combined in one or more examples, features, or embodiments. The term "patient" and "individual" may be used interchangeably herein. The terms "duct," "ostium," "opening," and "orifice," as used herein, may comprise an opening into a vessel and/or cavity of the body. It should be noted that although significant portions of the description of embodiments may be directed toward removal of a stone or other object lodged within a bile duct, embodiments are not limited to such uses, and claimed subject matter is intended to embrace various applications such as those involving other portions of the alimentary canal, other orifices and structures of a human patient, orifices and structures of an animal patient, intricate mechanical assemblies and/or structures, or any combination thereof.

A multi-lumen shaft may be used to form a removal device that may be operated in association with an endoscopic instrument to assist in removing an object, such as a stone lodged in one or more bile ducts, for example, from an individual. A stone or other object may be dislodged from a bile duct, for example, by urging the object toward an ostium or other opening, which may permit the object to pass through the opening and into the duodenum, for example. Responsive to entry into the duodenum, the object may be may be disposed of via normal discharge of solid waste from the human body, for example. Subsequent to entry of the object into the duodenum, the removal device may be stowed within an endoscopic instrument and the endoscopic instrument may be withdrawn from the body through the alimentary canal, for example.

A removal device, which may comprise a thermoplastic polyurethane expandable vessel, may be coupled to a polyurethane multi-lumen shaft, for example. A removal device may be conveyed through a working channel of an endoscopic instrument if an endoscopic device is appropriately positioned within a body cavity. A camera located at a distal end portion of an endoscopic instrument may be employed to provide imagery to a surgeon, for example, to inform the surgeon that a distal portion of an endoscopic instrument may be in position to deploy a removal device. A guide wire may be extended from the endoscopic device and advanced through an ostium, such as the hepatopancreatic ampulla. A multi-lumen shaft, which may comprise a polyurethane material, coupled to the guide wire may follow the inserted guide wire through an ostium, for example, and advanced to a location nearby a stone or other object to be removed. Contrast dye, which may be visible through a radioimaging device (i.e., x-ray machine, computer aided tomographic scanner, or the like) may be released from a multi-lumen shaft positioned proximate with an expandable vessel and may assist a surgeon in determining an approximate location of an object to be removed. At an appropriate time, a multi-lumen shaft may dispense a fluid under sufficient pressure to increase volume of an expandable vessel until the expandable vessel approaches a threshold volume. The expandable vessel may then be urged toward an ostium, in a manner that pushes the stone or other object through the ostium.

In embodiments, a multi-lumen shaft may be coupled to a thermoplastic urethane expandable vessel, for example, by way of a thermoplastic welding process. In embodiments, a thermoplastic welding process may give rise to fusing an expandable vessel to a cylinder-shaped polyurethane shaft at one or more circumferential locations of the shaft. Accordingly, an expandable vessel may be unlikely to separate from a polyurethane shaft thereby enhancing ease of removal of a stone or other object from an orifice.

Embodiments may represent a significant performance increase over conventional latex-based expandable vessels adhered to a multi-lumen shaft, for example. Latex-based vessels, for example, may be prone to breakage, leakage, and/or separation from a shaft to which a latex-based vessel may be attached. In particular conventional implementations, latex-based vessels may be affixed to a shaft using an adhesive. However, in many instances, an adhesive may not possess sufficient bond strength to resist shear and/or other stresses that may be encountered during inflation, and/or removal of objects from body orifices, for example. In response to breakage, leakage, and/or separation, which may occur in association with conventional stone or object removal procedures, a shaft and severed latex vessel may require removal from a patient so that another attempt at stone or other object removal may be performed.

Often, removal of a shaft may involve drawing of the shaft in a proximal direction through a working channel of an endoscopic device so that a new shaft and expandable vessel can be reinserted and advanced distally and into a patient's alimentary canal. The shaft and latex-based expandable vessel may be repositioned in an individual's alimentary canal and the object removal process may be reattempted. In many instances, this may give rise to an undesirable increase in surgeon and support staff time, an increase in equipment costs, and an increase patient discomfort. Accordingly, embodiments represented by claimed subject matter, which may involve use of a thermoplastic polyurethane inflatable vessel fused to a polyurethane multi-lumen shaft may represent an advantage over conventional processes by decreasing likelihood of breakage or separation, for example, of an expandable vessel. This may, in turn, reduce surgeon and support staff time, decrease equipment costs, and so forth.

A multi-lumen shaft coupled to an expandable vessel comprising material other than latex may also benefit healthcare workers, such as surgeons and support staff, involved in endoscopic procedures. For example, if an endoscopic surgeon or other individual involved in endoscopic procedures suffers from an allergy to latex, the individual may employ material handling practices to reduce exposure to latex-based materials. Further, patients who suffer from latex allergies may also experience inflammation and/or additional undesirable consequences in response to exposure to latex-based expandable vessels. Accordingly, use of medical implements coupled to thermoplastic polyurethanes, for example, may represent a means of avoiding such exposure, which may reduce undesirable consequences associated with exposure latex-based expandable vessels, for example.

A multi-lumen shaft may comprise a polyurethane material and one or more output ports for dispensing fluoroscopic contrast dye, which may permit a surgeon, radiologist, or other healthcare professional, for example, to observe areas proximate with an object to be removed. Observation of areas proximate with an object to be removed may be permitted, for example, by way of a fluoroscopic imaging device, such as an x-ray machine, computer aided tomography scanner, or the like. Dispensed contrast dye may also enable a surgeon, radiologist, or other healthcare professional to observe structures nearby an object to be removed, such as, for example, a biliary tree that may be distal from a stone or other object lodged in a bile duct.

In an embodiment, a shaft for use with an endoscopic instrument may comprise four lumens, which may be used to transport saline solution, for example, under sufficient pressure to inflate a thermoplastic urethane expandable vessel. Additional lumens may function to transport contrast dye at areas to two sides of a thermoplastic urethane expandable vessel. An additional lumen may be used to couple to a guide wire which may permit the shaft and expandable vessel coupled to the shaft to be accurately positioned at precise locations within a patient, for example.

According to one illustrative embodiment, as disclosed herein, a thermoplastic polyethylene expandable vessel may be welded to a cylinder-shaped polyurethane multi-lumen shaft. Saline solution, delivered by a multi-lumen shaft to an expandable vessel at a suitable pressure, may inflate a vessel to a diameter of, for example, between approximately 5.0 mm and approximately 25.0 mm. It has been observed that a thermoplastic polyethylene expandable vessel of approximately 5.0 mm to approximately 25.0 mm may be of sufficient girth to form a temporary seal such that, when drawn towards the ostium, for example, stones or other objects may be urged along the biliary duct, for example, through a patient's ampulla of vater (i.e., the hepatopancreatic ampulla) and into the patient's duodenum. Due at least in part to increased strength of an expandable vessel, such object removal may be performed in a single attempt.

FIG. 1 is a diagram of an embodiment 10 showing use of an endoscopic instrument and shaft deployed in an alimentary canal. In accordance with a conventional procedure involving an endoscopic instrument, endoscopic instrument 100, for example, may be advanced through a patient's alimentary canal while a patient is, for example, under sedation. Endoscopic instrument 100 may be advanced into a patient's mouth, into the patient's esophagus, through the cardia, stomach, and pyloric valve, for example, and into a patient's duodenum. It should be noted that embodiment 10 represents merely a single implementation of a multi-lumen shaft used in association with an endoscopic instrument, and claimed subject matter is not limited to any particular embodiment, such as that of FIG. 1. For example, a multi-lumen shaft may be used in association with endoscopic instruments and advanced into other body cavities, including body cavities of a human patient, animal patient, or into an intricate mechanical structure, or combinations thereof, for example. Further, implementations may involve the use of other medical instruments that may be used to view internal structures of living organisms and/or mechanical apparatuses, and claimed subject matter is not limited in this respect.

Endoscopic instrument 100 may include camera 103 which, for example, may provide visual feedback to assist an endoscopic surgeon in positioning an endoscopic instrument. Although not shown in FIG. 1, endoscopic instrument 100 may additionally comprise a lamp or other illumination source so as to enable lighting of body cavities, such as alimentary canal 135. Further, although not shown explicitly in FIG. 1, endoscopic instrument 100 may include a working channel that may permit tools, utensils, and other implements to be conveyed into, for example, a patient's alimentary canal and/or other body orifice. In the example of FIG. 1, endoscopic instrument 100 may be used to position multi-lumen shaft 140 to a location proximate with, for example, ostium 120. In an embodiment, ostium 120 represents an opening, such as the hepatopancreatic ampulla, through which guide wire 150 may be advanced.

If endoscopic device 100 is positioned proximate with ostium 120, a surgeon may advance guide wire 150 through ostium 120. Subsequent to penetration of ostium 120, multi-lumen shaft 140 may also be advanced through ostium 120. In an embodiment, advancement of guide wire 150 and/or multi-lumen shaft 140 may be enabled, at least in part, using camera 103 to obtain visual feedback of structures within, for example, alimentary canal 135.

Upon entry to biliary duct 105, by way of ostium 120, for example, multi-lumen shaft 140 may be at least partially advanced toward stone 125 and further (i.e., distally) into biliary duct 105. In embodiments, for example, one or more of distal multi-lumen shaft port 110 and proximal multi-lumen shaft 115 may be used to dispense fluoroscopic contrast dye, which may be used in conjunction with a fluoroscopic device, such as an x-ray machine, computer aided tomography scanner, or the like, to provide imagery to an endoscopic surgeon. In one exemplary embodiment, an endoscopic surgeon may locate ostium 120 by way of camera 103, and for example, upon observing the entry of guide wire 150 and at least a distal portion of multi-lumen shaft 140 into ostium 120, dispense a fluoroscopic contrast dye through, for example, distal multi-lumen shaft port 110. Fluoroscopic contrast dye, which may distribute within biliary duct 105, may enable a surgeon to position multi-lumen shaft 140 relative to stone 125. It should be noted, however, that some embodiments may involve positioning of a multi-lumen shaft without assistance from contrast dye, and claimed subject matter is not limited in this regard.

If positioned within biliary duct 105, such as, for example, shown in FIG. 1, multi-lumen shaft 140 may introduce saline solution into expandable vessel 130. Multi-lumen shaft 140 may be configured to be nonreactive with saline or other solution introduced into expandable vessel 130. Under an appropriate fluid pressure, expandable vessel 130 may expand in size until, for example, vessel 130 comes into contact with an inner circumference of biliary duct 105. Consequently, at least in some embodiments, expandable vessel 130 may form a temporary seal that may preclude contrast dye emanating from distal multi-lumen shaft port 110 to seep or leak towards ostium 120. Thus, contrast fluid may be permitted to fill biliary duct 105. Filling of biliary 105 with contrast dye may, for example, enable an endoscopic surgeon, radiologist, or other healthcare professional to observe more distal structures that may lie within and/or be in fluid communication with biliary duct 105 using, for example, a radioimaging device (e.g., an x-ray machine). Thus, additional structures such as the common bile duct, pancreatic duct, cystic duct, common hepatic duct, as well as other structures may be visible if expandable vessel is permitted to form a temporary seal of at least a portion of biliary duct 105. It should be noted, however, that liquids, such as contrast dye, emanating from distal multi-lumen shaft 110 may provide other benefits, and claimed subject matter is not limited in this respect.

As shown in FIG. 1, multi-lumen shaft 140 may additionally comprise proximal multi-lumen shaft port 115. In embodiments, proximal multi-lumen shaft port 115 may additionally be employed to dispense contrast dye within biliary duct 105, for example. Consequently, if permitted to at least partially surround stone 125, contrast dye may enable an endoscopic surgeon, radiologist, and/or other professional to monitor movement of stone 125, as expandable vessel 130 is drawn toward ostium 120. In some instances, it may be possible, for example, to observe the passing of stone 125 through ostium 120, and into alimentary canal 135. Again, however, use of contrast dye dispensed by way of distal multi-lumen shaft port 110 and/or proximal multi-lumen shaft port 115 represents one or more particular embodiments, and claimed subject matter is not limited in this respect. If stone 125 has emptied into alimentary canal 135, for example, expandable vessel 130 may be decreased in size, for example, by way of drawing saline solution from the expandable vessel and through multi-lumen shaft 140. Multi-lumen shaft 140 may then be retracted and stowed at a location internal to endoscopic device 100. Stowage of multi-lumen shaft 140 within endoscopic device 100 may permit an endoscopic surgeon, for example, to remove multi-lumen shaft 140 and expandable vessel 130 from a patient.

Figure 2A:
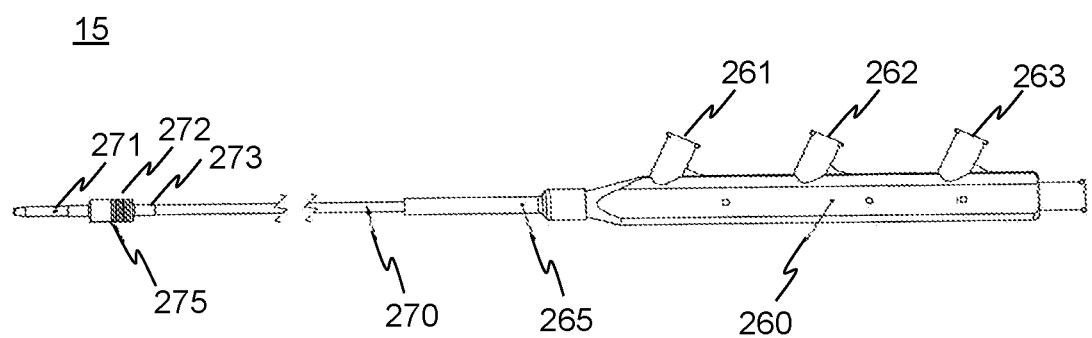
FIGS. 2A and 2B are diagrams of an embodiment of a multi-lumen shaft employed as a removal device.

FIG. 2A is a diagram of an embodiment of a multi-lumen shaft employed as a removal device 15. Removal device 15 may comprise, for example, polycarbonate manifold 260, polyolefin strain relief sheath 265, polyurethane multi-lumen shaft 270, and polyurethane expandable vessel 275. In embodiments, polyolefin strain relief sheath 265 may surround a portion of polyurethane multi-lumen shaft 270 in a manner that prevents or at least reduces likelihood of improperly bending or kinking polyurethane shaft 270 as shaft 270 and expandable vessel 275 are passed through a working channel of an endoscopic device, such as endoscopic device 100. In embodiments, polyurethane shaft 270 comprises a material that is nonreactive with radioimaging contrast dyes, saline solution, and/or other compressible or incompressible fluids that may be transported through polycarbonate manifold 260 and polyurethane shaft 270 for dispensing at a distal end portion of shaft 270, such as a location nearby expandable vessel 275, for example.

Polycarbonate manifold 260 may comprise one or more fluid coupling ports, such as fluid coupling ports 261, 262, and 263, for example. In an embodiment, fluid coupling port 261 may be used to inject radioimaging contrast dye to a distal portion of polyurethane shaft 270, such as, for example, distal output port 271. Likewise, fluid coupling port 262 may be used to inject saline solution or other fluid, under suitable pressure, to inflate expandable vessel 275 by way of, for example, medial output port 272 (which may be obscured from view by expandable vessel 275). Likewise, fluid coupling port 263 may be used to inject radioimaging contrast dye to a proximal output port, such as, for example, proximal output port 273.

Figure 2B:
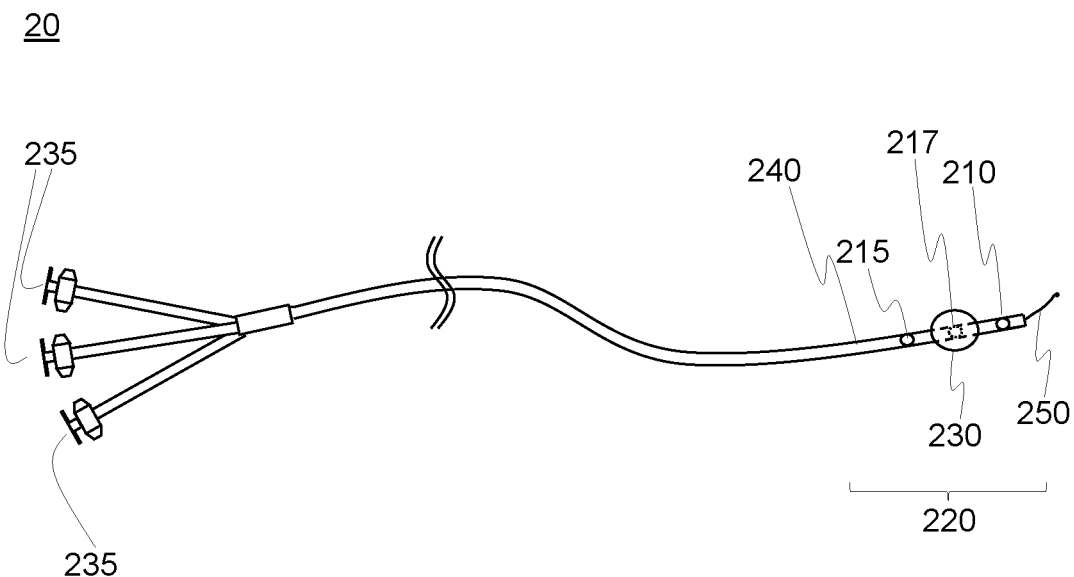

FIG. 2B is a diagram of an embodiment of a multi-lumen shaft used with the removal device. The removal device of FIG. 2 may be suitable, for example, for insertion into a working channel of an endoscopic instrument, such as endoscopic instrument 100 of FIG. 1. However, embodiment 20 may be suitable for insertion into other devices and/or instruments, and claimed subject matter is not limited in this respect. In embodiments, insertion of a multi-lumen shaft into a working channel of an endoscopic instrument begins, for example, with insertion of distal end portion 220. If situated within an endoscopic device, multi-lumen shaft 240 may be deployed, perhaps with the assistance of a camera, such as camera 103 shown in FIG. 1, to a location proximate with an ostium or other opening into a body cavity. Beginning with guide wire 250, multi-lumen shaft 240 may be inserted into an ostium.

If distal end portion 220 of multi-lumen shaft 240 can be positioned proximate with a stone or other object lodged in a body orifice, for example, medial multi-lumen shaft port 217 may dispense fluid, such as saline solution, which may increase volume of expandable vessel 230. Control for dispensing of saline solution may, for example, be provided by one or more of injector controls 235. As discussed with reference to FIG. 1, an expandable vessel may expand to form a temporary seal within a biliary duct or other structure. If at least a partial temporary seal can be formed, by way of expansion of expandable vessel 230 coming into contact an inner circumference of a biliary duct, for example, contrast dye may be dispensed from one or more of distal multi-lumen shaft port 210 and proximal multi-lumen shaft port 215. Dispensing of contrast dye from distal manifold port 210 may, for example, enable an endoscopic surgeon, radiologist, or other healthcare professional to observe imagery corresponding to additional structures located distally from multi-lumen shaft 240, for example. Dispensing of contrast dye may also permit real-time observation, by way of a fluoroscope (i.e., x-ray machine) of withdrawal of multi-lumen shaft 240 as well as urging of a stone or other object toward a patient's alimentary canal using expandable vessel 230, for example.

Figure 3:
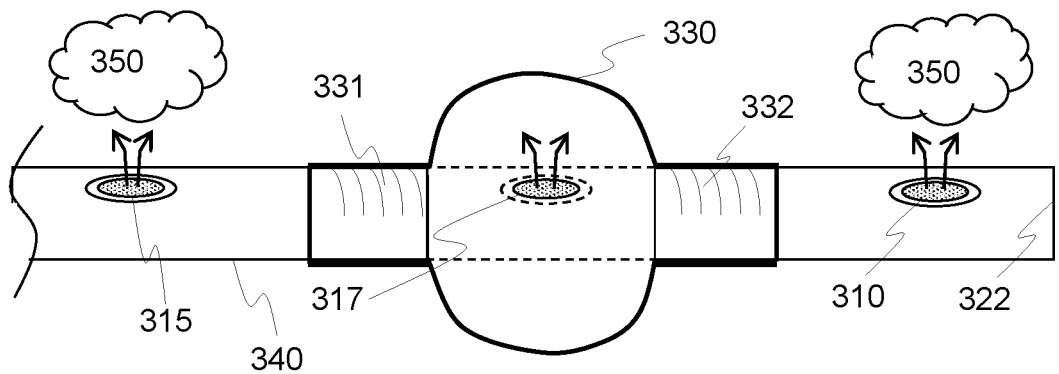
FIG. 3 is a diagram showing an embodiment of a multi-lumen shaft deploying an expandable vessel.

FIG. 3 is a diagram showing an embodiment of a multi-lumen shaft deploying an expandable vessel. In FIG. 3, multi-lumen shaft 340 may be advanced by guiding the multi-lumen shaft to follow a guide wire (not shown in FIG. 3) coupled to sealed end portion 322. Multi-lumen shaft 340 may be inserted into a working channel of an endoscopic instrument, such as endoscopic instrument 100 of FIG. 1, and inserted into a patient's alimentary canal, for example. If a multi-lumen shaft has entered a body orifice, such as an ostium (e.g., the hepatopancreatic ampulla), contrast dye 350 may be dispensed from one or more of distal multi-lumen shaft port 310 and proximal multi-lumen shaft port 315. Contrast dye may, at least in some embodiments, be employed to enable an endoscopic surgeon operating a fluoroscope to appropriately position multi-lumen shaft 340 proximate with a stone or other object for which removal may be desired. However, multi-lumen shaft 340 of FIG. 3 may be useful in a variety of other scenarios, such as removal of objects lodged at other locations of a patient, and may make possible object removal from other living organisms and/or mechanical structures. Claimed subject matter is intended to embrace all such uses of multi-lumen shaft 340.

At an appropriate time, multi-lumen shaft 340 may dispense saline solution into expandable vessel 330 way of multi-lumen shaft port 317. If dispensed under a suitable pressure, for example, expandable vessel 330 may gain in volume until expandable vessel 330 occupies at least a considerable cross-section of a body orifice such as biliary duct 105 of FIG. 1. Expandable vessel 330 may be fused by way of thermoplastic welding to multi-lumen shaft 340 at, for example, weld zones 331 and 332. In embodiments, use of thermoplastic polyurethane expandable vessels fused to polyurethane multi-lumen shafts, for example, may lessen a need for adhesive used for affixing expandable vessels of other compositions to multi-lumen shafts, such as shaft 340. In addition, use of thermoplastic polyurethane expandable vessels fused to polyurethane multi-lumen shafts may result, at least in part, in a much stronger bond than would result if latex expandable vessels were to be affixed, via an adhesive, to a polyurethane shaft.

Figure 4:
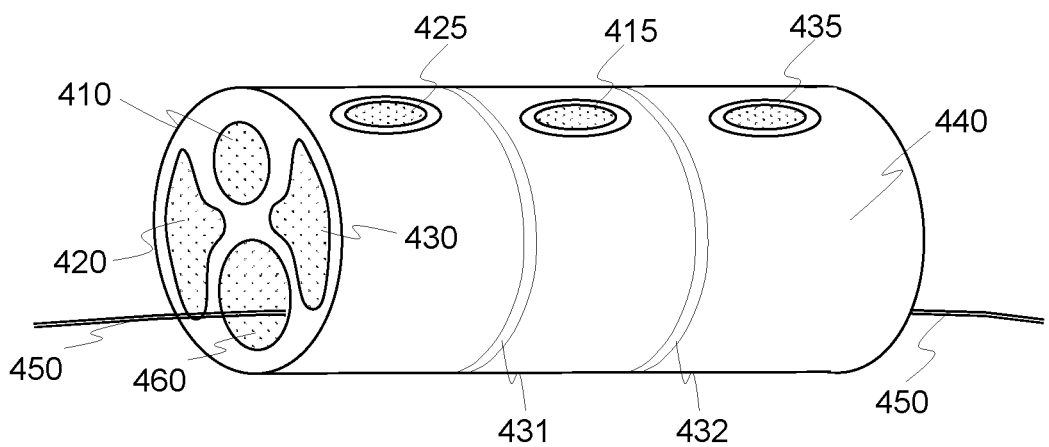
FIG. 4 is a diagram showing a cross-section of an embodiment of a multi-lumen shaft.

FIG. 4 is a diagram showing a cross-section of an embodiment of a multi-lumen shaft. In FIG. 4, multi-lumen shaft 440 may comprise first lumen 410, which may be used to transport fluid, such as saline solution, for dispensing at fluid output port 415. In FIG. 4, weld zone 431 and 432 of multi-lumen shaft 440 may be seen to the left and right of fluid output port 415. In embodiments, weld zones 431 and 432 correspond to locations along a circumference of multi-lumen shaft 440 at which an expandable vessel, such as expandable vessel 330 of FIG. 3, may be welded and/or fused to multi-lumen shaft 440. Fusing of an inflatable vessel, such as by way of thermoplastic welding, may permit an expandable vessel to be filled with fluid, such as saline solution, so as to form a temporary seal within an orifice, such as biliary duct 105 of FIG. 1, for example.

Multi-lumen shaft 440 may also include contrast dye port 425, located at a proximal end portion of multi-lumen shaft 440. In the embodiment of FIG. 4, contrast dye port 425 may be coupled to a second lumen 420 in a manner that permits contrast dye from second lumen 420 to be dispensed through contrast dye port 425, located at a proximal end portion of the multi-lumen shaft. Likewise, contrast dye port 435 may be coupled to third lumen 430 in a manner that permits contrast dye from third lumen 430 to be dispensed via contrast dye port 435. Multi-lumen shaft 440 may also comprise guide wire lumen 460 in a manner that permits multi-lumen shaft 440 to slide along guide wire 450.

Returning briefly to FIG. 2B, polycarbonate manifold 260 may comprise a polycarbonate structure suitable for use with, for example, medical equipment. Polycarbonate materials suitable for construction of a manifold may be purchased from suppliers such as Westlake Plastics Company, PO Box 127, Lenni, PA 19052 (www.Westlakepastics.com). However, alternative materials other than polycarbonate structures, for example, may comprise polycarbonate manifold 260. Considerations for selection of a material may include, for example, materials comprising a suitable flexural modulus, flexural strength, hardness (Rockwell) impact strength, tensile elongation, tensile strength, coefficient of thermal expansion, heat deflection temperature, and specific gravity.

Expandable vessels, such as described herein may comprise a thermoplastic polyurethane elastomer that may be partially or fully thermoplastic. In embodiments, an expandable vessel may comprise a linear segment block copolymer comprising "hard" and "soft" segments. A hard segment may comprise an aromatic or aliphatic material. Aromatic thermoplastic polyurethanes may be based on isocyanates such as methylene diphenyl diisocyanate and/or related compounds. Aliphatic thermoplastic polyurethanes may be based on isocyanates such as methylene dicyclohexyl diisocyanate (H12MDI). Isocyanates may be combined with short-chain diols to form a "hard" segment. It should be noted that these are merely examples of engineered thermoplastic polyurethanes that may be used to form an expandable vessel, however claimed subject matter is not limited in this regard.

FIG. 5 is a flow diagram of a process for using an embodiment of a multi-lumen shaft in association with an endoscopic procedure. The arrangement of components in FIG. 1 may be suitable for performing the method of embodiment 50. However, claimed subject matter is not limited to the particular implementation of any particular figure shown and described herein and alternate arrangements of components in other implementations may be used. Example embodiments, such as embodiment 50 shown in FIG. 5, may include blocks in addition to those shown and described, fewer blocks, blocks occurring in an order different than may be identified, or any combination thereof.

At 510, a multi-lumen shaft may be inserted into a location distal to an object for removal. 510 may be preceded by inserting a guide wire into an orifice, such as a bile duct, and dispensing fluoroscopic contrast dye in a manner that permits an endoscopic surgeon, for example, to observe a position of an object to be removed. At 520, and expandable vessel may be inflated until the expandable vessel forms a temporary seal which may, for example. At 530, contrast dye may be dispensed so as to permit radioimaging of additional structures, such as biliary tree, which may be coupled to a patient's bile duct. It should be noted, however, that 530 may be employed to enable radioimaging of other structures, and claimed subject matter is not limited in this respect. At 540, a multi-lumen shaft, which may be fused to an expandable vessel, be drawn toward an ostium or other opening in a manner that permits a stone or other object to empty into a patient's alimentary canal. Again, embodiments may permit the removal of other objects, which may be lodged at locations other than ducts coupled to the elementary canal, and claimed subject matter is not limited in this regard.

While there has been illustrated and/or described what are presently considered to be example features, it will be understood by those skilled in the relevant art that various other modifications may be made and/or equivalents may be substituted, without departing from claimed subject matter. Additionally, many modifications may be made to adapt a particular situation to teachings of claimed subject matter without departing from one or more central concept(s) described herein. Therefore, it is intended that claimed subject matter not be limited to particular examples disclosed, but that claimed subject matter may also include all aspects falling within appended claims and/or equivalents thereof.

What is claimed is:

1. A method of dislodging an object behind an ostium, comprising:
    inserting a multi-lumen shaft into a duct and a location distal to the object;
    inflating an expandable vessel, coupled to multi-lumen shaft, until the expandable vessel approaches a threshold volume;
    dispensing a fluoroscopic contrast dye through a port of the multi-lumen shaft at a location proximal to the expandable vessel; and
    dispensing a fluoroscopic contrast dye through a port of the multi-lumen shaft at a location distal to the expandable vessel.

2. The method of claim 1, further comprising the step of drawing the multi-lumen shaft towards the ostium until the object passes the ostium.

3. The method of claim 1, wherein the step of inflating of the expandable vessel comprises dispensing a saline solution to the expandable vessel.

4. The method of claim 1, wherein the expandable vessel is composed of polyurethane.

5. The method of claim 1, wherein the step of inflating of the expandable vessel in a duct will block fluid communication in the duct between the port of the multi-lumen shaft at a location proximal to the polyurethane expandable vessel and the port of the multi-lumen shaft at a location distal to the polyurethane expandable vessel.

* * * * *